United States Patent [19]

Maslov et al.

[11] 4,171,996
[45] Oct. 23, 1979

[54] FABRICATION OF A HETEROGENEOUS SEMICONDUCTOR STRUCTURE WITH COMPOSITION GRADIENT UTILIZING A GAS PHASE TRANSFER PROCESS

[75] Inventors: Vadim N. Maslov; Oleg E. Korobov; Alla N. Lupacheva; Alexandr N. Vlasov, all of Moscow; Viktor V. Myasoedov, Podolsk Moskovskoi oblasti; Ellin P. Bochkarev, Moscow; Felix A. Gimelfarb, Moscow; Izidor K. Bronshtein, Moscow; Natalya I. Lukicheva, Moscow; Evgeny V. Sinitsyn, Moscow; Jury V. Sokurenko, Moscow; Elena S. Jurova, Moscow; Elena M. Kistova, Moscow; Marina A. Konstantinova, Moscow; Veniamin M. Samaginov, Moscow, all of U.S.S.R.

[73] Assignee: Gosudarstvenny Nauchno-Issledovatelsky i Proektny Institut Redkonetallicheskoi Promyshlennosti "Giredmet", Moscow, U.S.S.R.

[21] Appl. No.: 930,536

[22] Filed: Aug. 1, 1978

Related U.S. Application Data

[62] Division of Ser. No. 712,324, Aug. 6, 1976, Pat. No. 4,117,504.

[30] Foreign Application Priority Data

Aug. 12, 1975 [SU] U.S.S.R. ............... 2157007[I]
Nov. 5, 1975 [SU] U.S.S.R. ............... 2184251
Mar. 25, 1976 [SU] U.S.S.R. ............... 2339635

[51] Int. Cl.² .................. H01L 21/20; H01L 29/14
[52] U.S. Cl. .................. 148/175; 29/572; 29/576 E; 29/580; 148/1.5; 148/174; 156/611; 156/613; 357/16; 357/88

[58] Field of Search ............... 148/175, 1.5, 174; 156/611, 613; 29/572, 576 E, 580; 357/16, 17, 18, 30, 88

[56] References Cited

U.S. PATENT DOCUMENTS

| 3,291,657 | 12/1966 | Sirtl | 148/175 |
| 3,359,143 | 12/1967 | Heywang et al. | 148/174 |
| 3,425,878 | 2/1969 | Dersin et al. | 148/175 X |
| 3,428,500 | 2/1969 | Maeda | 148/175 |
| 3,441,453 | 4/1969 | Conrad et al. | 148/175 |
| 3,493,444 | 2/1970 | Sirtl et al. | 148/175 |
| 3,893,876 | 7/1975 | Akai et al. | 148/175 |
| 3,925,118 | 12/1975 | Hollan | 118/48 X |

OTHER PUBLICATIONS

Yoshikawa et al., "Optical Properties of Hetero-Epitaxial CdS Films", Japanese J. Applied Physics, vol. 13, No. 9. Sep. 1974, pp. 1353–1361.

*Primary Examiner*—L. Dewayne Rutledge
*Assistant Examiner*—W. G. Saba
*Attorney, Agent, or Firm*—Haseltine, Lake & Waters

[57] ABSTRACT

A method for producing a heterogeneous semiconductor structure with a composition gradient in which a semiconductor material is transferred through the gaseous phase onto the substrate from a source comprising the two AB and AC components and including a number of parallel strips, each of said strips having a constant ratio between the AB and AC components. At first, the source is gradually brought under the substrate at a speed chosen within the range of 100 cm per hour to 0.1 cm per hour, bringing first the strip of the source, which has a maximum content of the AB component. As all the strips have been brought under the substrate, the source is stopped for a period of time required for the formation of the main layer of a required thickness.

3 Claims, 12 Drawing Figures

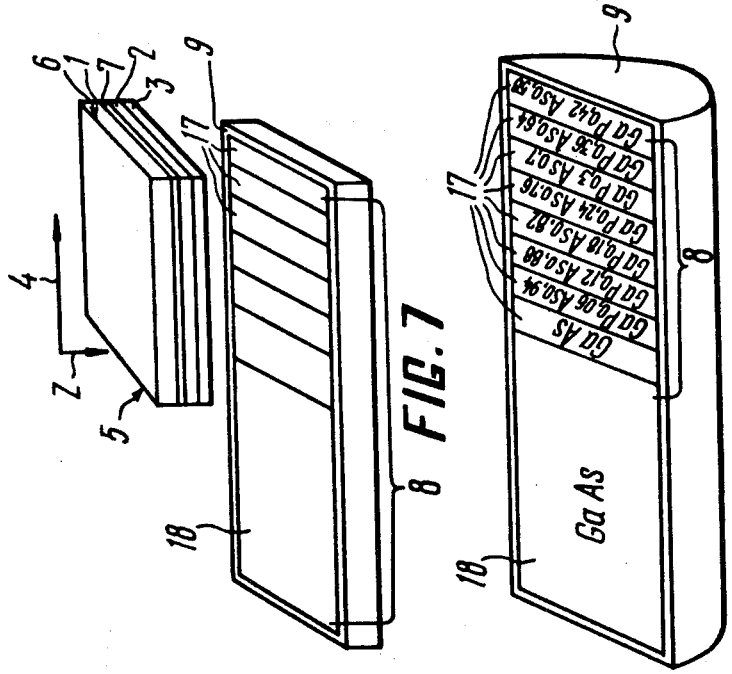
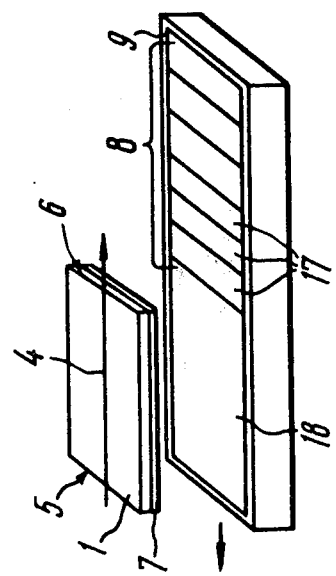
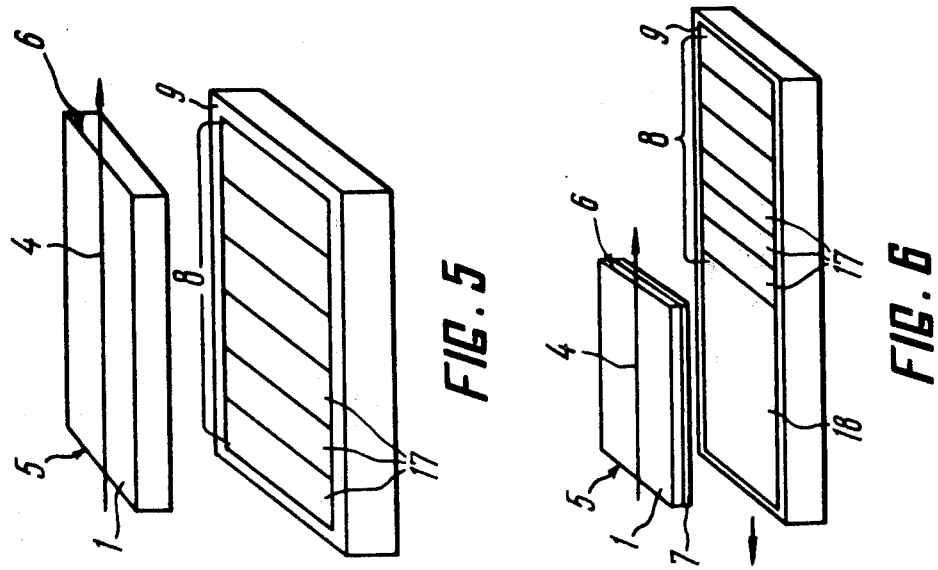

FABRICATION OF A HETEROGENEOUS SEMICONDUCTOR STRUCTURE WITH COMPOSITION GRADIENT UTILIZING A GAS PHASE TRANSFER PROCESS

This is a division of application Ser. No. 712,324 filed Aug. 6, 1976 and now U.S. Pat. No. 4,117,504.

BACKGROUND OF THE INVENTION

The present invention relates to semiconductor instruments and, more particularly, to a heterogeneous semiconductor structure with a composition gradient, and a method for producing same.

The invention can find extensive application in producing semiconductor lasers with an adjustable generation wavelength, and semiconductor spectrometers of high resolving power.

Such instruments, produced on the basis of the proposed heterogeneous semiconductor structure with a composition gradient, may be used in such fields as laser spectroscopy of substances for fundamental research, high-sensitivity remote checking of the composition of fumes, gas mixtures and solutions, while controlling production processes, in the analysis of exhaust gases of automobiles, laser photochemistry, and in the metrology of laser irradiation.

In addition, the heterogeneous semiconductor structure with a composition gradient in accordance with the present invention can be employed in devices for high-sensitivity remote detection of substances which pollute the environment, as well as in contactless sensors for checking chemical compositions to be used in automatic production control systems, light-emitting instruments and optoelectronic and integral optics devices.

An important application of the proposed heterogeneous semiconductor structure with a composition gradient is to high-sensitivity hydrostatic pressure gauges.

Such sensors, provided with a sensitive element on the basis of the proposed heterostructure, are marked by a broader range of measurements (of 10 to 60,000 bars), as compared to conventional types of sensors.

Novel sensors on the basis of the present invention may find extensive application in automatic control and check systems, as well as in different fields of industry and research, such as the synthesis of diamonds, pressure measurements in drill holes and explosion chambers, measurements of the pressure produced by rock beds in seismic zones, weighing of heavy loads (railroad cars, trucks, machinery), and in other fields of endeavor which call for hydrostatic pressure measurements over a broad range.

There is known a heterogeneous semiconductor structure comprising a substrate coated with a first reflecting layer, and a main semiconductor layer arranged on the first reflecting layer, said main semiconductor layer being solid solution of $AB_xC_{1-x}$. The solid solution is composed of binary compounds with the general formulas AB and AC, whereas x represents the molar fraction of the AB compound in the solid solution $AB_xC_{1-x}$, which is limited by the ratio $0 \leq x \leq 1$.

The semiconducting compounds AB and AC comprising one common chemical element denoted by letter A and variable content components denoted by letters B and C, respectively, are selected from the following pairs of elements: $A^{II}B^{VI}$ and $A^{II}C^{VI}$; $A^{III}B^{V}$ and $A^{III}C^{V}$; $B^{III}A^{V}$ and $C^{III}A^{V}$; $B^{II}A^{VI}$ and $C_{II}A^{VI}$; $B^{IV}A^{VI}$ and $C^{IV}A^{VI}$; so that said pairs of binary compounds form the following solid solutions respectively; $A^{II}B_x^{VI}C_{1-x}^{VI}$, $A^{III}B_x^{V}C_{1-x}^{V}$, $B_x^{III}C_{1-x}^{III}A^{V}$, $B_x^{III}C_{1-x}^{III}A^{V}$, $B_x^{IV}C_{1-x}^{IV}A^{VI}$, where $B^{II}$, $A^{III}$, $A^{V}$ and $A^{VI}$ are elements of Groups II-B, III-A, V-A and VI-B, respectively, of the Periodic Table; $B^{II}$ and $C^{II}$ are two different elements of Group II-B, $B^{III}$ and $C^{III}$ are two different elements of Group III-A; $B^{IV}$ and $C^{IV}$ are two different elements of Group IV-A; $B^{V}$ and $C^{V}$ are two different elements of Group V-A; and $B^{VI}$ and $C^{VI}$ are two different elements of Groups VI-A of the Periodic Table, and "x" varies from 0 to 1.

The composition of the main semiconductor layer changes gradually and continuously along the main axis from a maximum concentration of the AB component near the first edge of the main semiconductor layer to a maximum concentration of the AC component close to the opposite edge of the main semiconductor layer. A second reflecting layer is arranged on the outer surface of the main layer. The AB and AC components are semiconductor compounds having similar crystallographic properties. The known heterogeneous semiconductor structure is produced on the basis of solid solution of $CdSe_xS_{1-x}$ composed of binary compounds $CdSe(A^{II}B^{VI})$ and $CdS(A^{II}C^{VI})$.

The foregoing heterogeneous structure with a composition gradient is used in the main as the working irradiating element of a semiconductor laser with optical or electron excitation and an adjustable generation wavelength.

Working elements of lasers of this type can only operate when the material of the substrate is similar in its crystallographic properties (e.g., the parameters of the crystal lattice, the thermal expansion coefficient) to the solid solution $AB_xC_{1-x}$ of the main semiconductor layer.

As a result, the known heterogeneous semiconductor structure with a composition gradient can only be produced from an extremely limited range of semiconductor components with similar crystallographic parameters which do not differ to a great extent from the crystallographic parameters of the substrate material.

Such components are, for example, CdSe and CdS which have similar crystallographic properties. On the basis of these components there may be produced a working element of a laser operating within a range of wavelengths of 0.5 to 0.7 mu.

However, in a number of cases the formation of a heterogeneous structure for a laser irradiating in a different spectral range, or a laser with an extended generation wave adjustment range, or a working element of a laser which is supposed to be highly resistant to external effects, calls for the use of different semiconductor compounds whose crystallographic properties may be different.

The use of such components for the formation of the known type of heterostructure results in numerous imperfections of the crystal structure (dislocations, mechanical stresses, cracks) which, in the course of operation of the laser element, act upon a number of radiationless recombination centers and thereby either suppress the laser irradiation or worsen the irradiation characteristics of the laser.

While using the known heterogeneous structure, it is impossible to avoid the harmful effects of the substrate upon the main semiconductor layer which is composed of components with different crystallographic properties.

There is known a method for producing the above type of heterogeneous structure with a composition gradient, which structure is solid solution of $AB_xC_{1-x}$. According to this method, semiconductor components are transferred through the gas phase to the surface of the substrate which is heated to a temperature above 450°. The semiconductor components are transferred from a source whose temperatures is different from that of the substrate. The components enter the gas phase so that along the main axis of the semiconductor layer being formed, there is a continuous and gradual change in the concentration of atoms of B and C from a maximum concentration of B atoms near the first edge of the main semiconductor layer being formed to a maximum concentration of C atoms close to the opposite edge of this layer.

The semiconductor elements are directed to the gas phase from a source comprising two portions, the first being of the AB component, while the second is of the AC component. The continuous and gradual alteration of the composition is ensured by partially mixing AB and AC in the gas phase; a slit mask moving along the main axis of the substrate additionally provides for a continuous change in the thickness of the main layer along said axis from maximum to minimum.

The major disadvantage of the foregoing method for producing a heterogeneous semiconductor structure with a composition gradient resides in the fact that it does not always ensure a monocrystalline structure of the main semiconductor layer; on the contrary, it often results in the formation of a polycrystal which does not meet the requirements imposed by the laser irradiation, becase the polycrystalline structure accounts for numerous defects which, in the course of operation of the laser element, act upon a number of radiationless recombination centers and thus either suppress the laser irradiation or seriously affect the radiation characteristics of the laser.

For decrystallization purposes, the polycrystalline heterostructure is subjected to tempering at a high temperature. This operation makes the process complicated and lengthy and, although affecting the out, does not rule out completely all the defects that hinder the normal work of the laser.

Besides, the known method does not make it possible to produce a monocrystalline semiconductor heterostructure with a required rate of the change in the concentration of the components along the main axis. From the portions of the source, the compounds AB and AC propagate concentrically in relation to the centers of said portions; hence, a linear change in the components' concentration is ensured only in a narrow zone of the main layer being produced, which zone is close to the projection of the axis between the centers of the source's portions; it is impossible to produce a different type of change in the gradient value, while using the above type of source.

As a result, on the basis of the known heterogeneous structure, it is impossible to produce a working element of a laser with a required uniform adjustment of the generation wavelength within a broad range of wavelengths.

The known method for producing a heterogeneous semiconductor structure with a composition gradient is also disadvantageous in that on the basis of the structure it is supposed to produce, it is impossible to provide a working element of a laser having mirror layers on the side faces of the main semiconductor layer and also having a greater radiating power, as compared to known laser elements.

Such an element can only be produced on the basis of a heterogeneous structure with a constant direction of the composition gradient over the entire area of the semiconductor layer from one edge of said layer to the other. On the other hand, the known method makes it possible, as stated above, to provide a constant direction of the gradient only in a narrow zone near to the projection upon said layer of the axis between the centers of the source's portions.

Still another important drawback of the known method under review is the fact that it is impossible to control the process of doping the main semiconductor layer along the main axis and at a perpendicular to the latter. This factor limits the sphere of application of the known structure, since the radiation characteristics of the laser cannot in this case be optimized by providing for a variable doping level along the main axis, which level should correspond to the gradual change in the composition of the main semiconductor layer.

Finally, the known method does not make it possible to control the distribution of doping impurities over the thickness of the heterostructure, i.e. in the direction perpendicular to that of the composition gradient in the main semiconductor layer. As a result, the heterostructure cannot be used for working elements of other instruments.

It is an object of the present invention to provide a heterogeneous semiconductor structure with a composition gradient, which would be marked by a substantially reduced harmful effect of the substrate upon the crystalline structure and luminescent properties of the main semiconductor layer.

Thus, it is an object of the invention to provide a heterogeneous semiconductor structure with a composition gradient, which, when used as the working element of a laser, would improve the latter's radiation characteristics, i.e. reduce the density of the threshold current required to excite laser generation, as well as would improve the efficiency of converting the excitation energy into the luminous energy of the laser.

It is another object of the present invention to expand the range of compounds to be used for the formation of the main semiconductor layer, which would make it possible to select the components of the main layer from different classes of semiconductor compounds and, as a result, produce a series of heterogeneous structures to be used as working elements of lasers and photodetectors operating within a broad range of wavelengths, from the near-ultraviolet region to the infrared region.

It is also an important object of the invention to provide a heterogeneous semiconductor structure with a composition gradient, which would make it possible to raise the radiated power of lasers.

It is still another important object of the invention to provide a heterogeneous structure with an extremely small value of the composition gradient (a few mole percent per centimeter of length along the axis), which ensures a high accuracy of selecting a desired radiation wavelength of a reference laser.

It is yet another object of the invention to provide a heterogeneous structure, wherein the law of a change in the doping impurities would be independent of the law of a change in the composition of the main semiconductor layer, i.e. a heterostructure marked by a constant doping level both throughout the surface and volume of the main semiconductor layer, which would ensure a constant radiated power over the entire range of wavelengths.

Apart from the above, it is an object of the present invention to provide a method for producing the foregoing type of heterogeneous semiconductor structure with a composition gradient, which would ensure a broad range of continuous change in the composition of the main semiconductor layer of said structure (to a few tens of mole percent).

It is a further object of the invention to provide a method for producing a heterogeneous semiconductor structure, which method would make it possible to ensure a high accuracy of maintaining a predetermined composition gradient over the surface of the heterostructure, as well as the rectilinearity of the lines of the constant composition on the surface of the heterogeneous structure.

It is also an object of the invention to provide a method for producing a heterogeneous semiconductor structure with a composition gradient, which would make it possible to control the composition of said structure both over its surface and thickness in the course of producing said structure.

It is a further object of the invention to provide a method for the production of a heterogeneous semiconductor structure, which would make it possible to control the change in the doping impurity content irrespective of the change in the composition along the main axis in the course of producing said structure.

It is an object of the invention to provide a method for producing a heterogeneous semiconductor structure with a composition gradient, which structure can be employed as a working element of a laser without being subjected to thermal treatment.

Finally, it is an object of the invention to provide a simple source for carrying out the proposed method of producing a structure possessing all the abovementioned properties.

SUMMARY OF THE INVENTION

The foregoing and other objects of the present invention are attained by providing a heterogeneous semiconductor structure with a composition gradient, which comprises a monocrystalline substrate and a main semiconductor layer arranged on said substrate, said main layer being of doped solid solution of $AB_xC_{1-x}$ of semiconductor compounds AB and AC, where x, limited by the ratio $0 \leq x \leq 1$, designates molar fractions of the AB component in the solid solution of $AB_xC_{1-x}$ of the main layer having a composition gradient with a constant direction that is parallel to a main axis pre-selected on the surface of the substrate, which means a continuous change in the composition of the main layer along said axis from the portion of the layer which corresponds to a maximum content of the AB component of the solid solution to the portion of the layer corresponding to a maximum content of the AC component of the solid solution, said heterostructure further comprising, in accordance with the invention, a transition layer in the form of a doped solid solution of $AB_xC_{1-x}$, which transition layer is found between the substrate and the main semiconductor layer, the substrate being of a material whose crystallographic properties are similar to those of the AB component of the solid solution, the composition of the transition layer continuously changing along the main axis from the portion of the transition layer with a maximum content of the AB component to the portion corresponding to a maximum content of the AC component in the direction which is perpendicular to the surface of the substrate, from the composition of the main layer on the boundary with the transition layer to the composition having a maximum content of the AB component of the boundary with the substrate.

It is expedient that the heterogeneous structure of the present invention should include an additional semiconductor layer of doped solid solution of $AB_xC_{1-x}$ with a maximum content of the AB component, which additional layer is arranged between the transition layer and the substrate.

It is also expedient that the main, transition and additional layers be doped with a donor impurity producing shallow energy states to a concentration of free electrons of $5 \cdot 10^{17}$ to $7 \cdot 10^{18}$ cm$^{-3}$.

It is desirable that the heterogeneous semiconductor structure should be produced on the basis of a solid solution of $GaP_xAs_{a-x}$, where x is limited by the ratio $0 \leq x \leq 0.4$; the main semiconductor layer must be doped in this case with a donor impurity producing shallow energy states to a concentration of free electrons of $8 \cdot 10^{17}$ to $7 \cdot 10^{18}$ cm$^{-3}$; the transition layer must be simultaneously doped with an impurity producing shallow energy states and an impurity producing deep-lying energy states to a concentration of free electrons below $10^{14}$ cm$^{-3}$.

The objects of the present invention are also attained by providing a method for producing a heterogeneous semiconductor structure, according to which method a semiconductor compound is transferred through the gaseous phase onto the surface of the substrate, said substrate being heated to above 450°, from a source composed of two component, AB and AC, and a doping impurity, the temperatures of said source and said substrate being different, the semiconductor compound being transferred onto the surface of the substrate, according to the invention, from a nearby solid source comprising a plurality of adjacent main strips that are parallel to the edges of the source, each of said strips having a constant AB to AC ratio of its own, the width of each of said strips being less than or equal to the doubled distance between the surface of the source and that of the substrate, the first strip, located at the first edge of the source, having a maximum content of the AB compound, whereas the strip found at the second edge of the source has a maximum content of the AC compound, the ratio between the AB and AC compounds in two adjacent strips being changed by a value equal to the quotient of the division of the required value of the composition gradient of the main semiconductor layer by the width of said adjacent strips, the strips of said source being first gradually brought under the substrate by progressively moving along the main axis and in parallel with the surface of the substrate at a speed between 100 cm per hour and 0.1 cm per hour, beginning with the first strip of the source, having a maximum content of the AB compound, the source being stopped under the substrate after all the strips have been brought thereunder, for a period of time required for the formation of the main semiconductor layer.

In the case of forming a heterogeneous structure with an additional semiconductor layer, it is preferable that the transfer of the semiconductor compound onto the surface of the substrate should be carried out from a source comprising an additional strip whose width is at least equal to the length of the substrate along the main axis, which additional strip is adjacent to the first of said main strips and has a constant composition with a maximum content of the AB component. Prior to gradually bringing the main strips of the source under the substrate, the additional strip is brought under said substrate and stays there for a period of time required for the formation on the substrate of an additional layer of a desired thickness.

When forming a heterogeneous structure on the basis of solid solution of $GaP_xAs_{1-x}$, it is equally expedient that the transfer of the semiconductor compound onto the surface of the substrate should be carried out from a source comprising GaP and GaAs and having an additional group of strips located beyond said main strips, the composition and number of said additional strips corresponding to the composition and number of the main strips; the material of the additional strips must be doped with an impurity producing shallow energy states to a concentration of free electrons of $8 \cdot 10^{17}$ to $7 \cdot 10^{18}$ cm$^{-3}$. The material of the main strips should be doped to a level of $1 \cdot 10^{17}$ cm$^{-3}$. The gradual bringing of the main strips under the substrate is accompanied by additionally doping the heterogeneous structure being produced from the gas phase with an impurity producing deep-lying energy states. After all the main strips of the source have been brought under the substrate, the additional doping is discontinued, and the strips of the additional group are brought under the substrate to stay there for a period of time required for the formation of the main semiconductor layer of a predetermined thickness.

BRIEF DESCRIPTION OF THE DRAWINGS

Other objects and advantages of the present invention will become more apparent from the following detailed description of preferred embodiments thereof taken in conjunction with the accompanying drawings, wherein:

FIG. 5 shows the mutual positioning of the source and the substrate, in accordance with the invention;

FIG. 6 shows another way of mutually positioning the source and the substrate, in accordance with the invention;

FIG. 7 shows still another mutual positioning of the source and the substrate, in accordance with the invention;

FIG. 9 is a view of a source for producing said semiconductor heterostructure for lasers with a composition gradient on the basis of $GaP_xAs_{1-x}$ in accordance with the invention;

DESCRIPTION OF THE PREFERRED EMBODIMENTS

Consider now the proposed heterogeneous semiconductor structure with a composition gradient.

Figure 1:
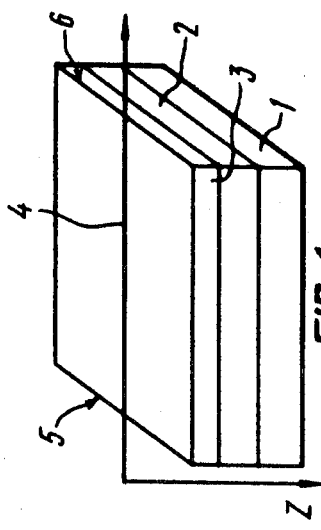
FIG. 1 is a schematic view of the heterogeneous structure with a composition gradient in accordance with the invention.

The heterogeneous structure of the present invention comprises a substrate 1 (FIG. 1) which is a plate of a material of a monocrystalline structure. The thickness of the substrate 1 is 100 to 500$\mu$.

According to the invention, on said substrate 1 there is arranged a transition semiconductor layer 2, whereupon there is arranged a main semiconductor layer 3.

The main semiconductor layer 3 is solid solution of the general formula $AB_xC_{1-x}$, composed of binary compounds of the general formulas AB and AC; x is the molar fraction of the compound AB in the solid solution of $AB_xC_{1-x}$, limited by the ratio $0 \leq x \leq 1$.

The semiconducting compounds AB and AC comprising one common chemical element denoted by letter A and variable content components denoted by letters B and C, respectively, are selected from the following pairs of elements: $A^{II}B^{VI}$ and $A^{II}C^{VI}$; $A^{III}B^V$ and $A^{III}C^V$; $B^{III}A^V$ and $C^{III}A^V$; $B^{II}A^{VI}$ and $C^{II}A^{VI}$; $B^{IV}A^{VI}$ and $C^{IV}A^{VI}$: so that said pairs of binary compounds form the following solid solutions respectively: $A^{II}B_x{}^{VI}C_{1-x}{}^{VI}$, $A^{III}B_x{}^VC_{1-x}{}^V$, $B_x{}^{III}C_{1-x}{}^{III}A^V$, $B_x{}^{II}C_{1-x}{}^{II}A^{VI}$, $B_x{}^{IV}C_{1-x}{}^{IV}A^{VI}$, where $A^{II}$, $A^{III}$, $A^V$ and $A^{VI}$ are elements of Groups II-B, III-A, V-A and VI-A, respectively, of the Periodic Table; $B^{II}$ and $C^{II}$ are two different elements of Group III-A; $B^{IV}$ and $C^{IV}$ are two different elements of Group IV-A; $B^V$ and $C^V$ are two different elements of Group V-A; and $B^{VI}$ and $C^{VI}$ are two different elements of Group VI-A of the Periodic Table, and "x" varies from 0 to 1.

The composition of the main semiconductor layer 3 changes gradually and continuously along an arbitrarily selected main axis 4, which is parallel to the surface of the main layer 3, from a maximum concentration of the AB component near a first edge 5 of the main semiconductor layer 3 to a maximum concentration of the AC component close to a second (opposite) edge 6 of the layer 3. The semiconductor transition layer 2 is also of a solid solution of $AB_xC_{1-x}$, whose composition changes gradually and continuously along the same main axis 4 from the portion corresponding to a maximum content of the AB component to the portion corresponding to a maximum content of the AC component.

In addition, the composition of the layer 2 is changed along the Z axis which is perpendicular to the surface of the main semiconductor layer 3, the change being from the composition of the main layer 3 near the surface adjacent to the transition layer 2 to the composition of $AB_xC_{1-x}$ whose crystallographic properties are the closest to those of the material of the substrate 1.

The substrate 1 may be produced from any material of a monocrystalline structure selected from the following semiconductor compounds: $A^{III}B^V$, $A^VB^{III}$, $A^{II}B^{VI}$, $A^{VI}B^{II}$, $A^{VI}B^{IV}$, as well as germanium and such dielectric materials as sapphire, beryllium oxide and magnesium oxide.

The main semiconductor layer 3 of the proposed heterogeneous structure is doped with a donor impurity to reach a concentration of free electrons from $5 \cdot 10^{17}$ to $7 \cdot 10^{18}$ cm$^{-3}$.

This donor impurity for the $A^{III}B^V$ compounds may be S, Se and Te.

The selection of the above-mentioned doping level is due to the fact that with a concentration of free electrons in the layer 3 below $5 \cdot 10^{17}$, the density of electron states of the main semiconductor layer 3 of the heterogeneous structure is insufficient to ensure a required radiation intensity if the proposed heterogeneous structure is used as the working element of a laser. If the donor doping level is above $7 \cdot 10^{18}$, this impairs the morphology of the working surface of the main semiconductor layer 3 and leads to an increased number of structural defects (vacancies, dislocations), which, in turn, affects the radiation characteristics of the laser.

According to the invention, the heterogeneous semiconductor structure with a composition gradient may be provided with an additional semiconductor layer 7 (FIG. 2) located between the substrate 1 and the transition semiconductor layer 2.

The additional semiconductor layer 7 comprises the $AB_xC_{1-x}$ component whose crystallographic properties are the closest to those of the material of the substrate 1.

The thickness of the additional semiconductor layer 7 is selected to be between 1 and 15μ.

A thickness of the layer 7 less than 1μ cannot provide for full compensation of defects which originate at the initial period of epitaxial growth of the layer 7 on the surface of the substrate 1.

If the additional layer 7 is more than 15μ thick, this will only result in an unjustifiably high semiconductor material consumption for further growth of the layer 7, without producing any positive effect.

A thickness of the layer 7 of 1 to 15μ guarantees complete elimination of the defects of the initially formed heterogeneous structure.

The thickness of the semiconductor layer 2 is between 5 to 100μ.

A thickness of the layer 2 of less than 3μ cannot reduce critical compressive stresses due to a certain difference in the parameters of the substrate 1 and the main semiconductor layer 3 of the heterogeneous structure.

A thickness of the layer 2 of more than 100μ only causes an increased consumption of the semiconductor material, without reducing the critical compressive stresses.

The main semiconductor layer 3 of the heterogeneous structure may be 5 to 50μ thick, depending upon the required penetration depth of excitation electrons, while generating laser radiation with a beam of fast electrons, if the heterogeneous structure is intended to be used as the working element of a laser.

Besides, the selection of a thickness of said layer 3 is determined by the required depth of the p-n junction, if the heterogeneous structure is meant to be used as the working element of a spectrophotometer.

Figure 3:
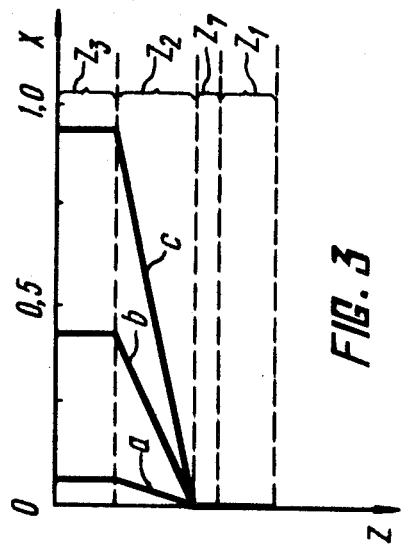
FIG. 3 shows the relationship between x and the thickness of the proposed heterogeneous structure along the Z axis.

The curves of FIG. 3 show the relationship between x and the thickness of the heterogeneous structure along the Z axis. $Z_3$ is the thickness of the main semiconductor layer 3 of the heterogeneous structure; $Z_2$ is the thickness of the transition layer 2; $Z_7$ is the thickness of the additional layer 7; $Z_1$ is the thickness of the substrate 1. The curve "a" shows the x(Z) relationship on section I—I of FIG. 2; the curve "b" (FIG. 3) shows the x(Z) relationship on section II—II of FIG. 2; the curve "c" (FIG. 3) shows the x(Z) relationship on section III—III of FIG. 2.

According to the invention, a heterogeneous structure with a composition gradient (FIG. 2) can be composed, for exmple, of GaAs and GaP; in this case, the main semiconductor layer 3 is of solid solution of GaP$_x$·As$_{1-x}$, where x is selected on the basis of this relationship: $0 \leq x \leq 0.4$. This heterogeneous structure may be used as the working element of a pressure gauge.

The main semiconductor layer 3 of this heterostructure is doped with a donor impurity to reach a concentration of free electrons of $8 \cdot 10^{17}$ to $7 \cdot 10^{18}$.

The above doping level is selected on the assumption that with a concentration of carriers below $8 \cdot 10^{17}$, the density of electron states in the main semiconductor layer 3 is insufficient to ensure the required thermal stability of the sensitivity factor of a pressure gauge.

Concentrations of carriers in excess of $7 \cdot 10^{18}$ impair the morphology of the working surface of the main semiconductor layer 3 and account for increasing numbers of such structural defects as vacancies and dislocations, which factor substantially reduces the sensitivity of a pressure gauge.

The transition semiconductor layer 2 is additionally doped with impurities, producing deep-lying energy states, to a level at which the resistivity of the transition semiconductor layer 2 is at least 1,000 times as great as that of the main layer 3.

The additional layer 7 is 1 to 5μ thick; the thickness of the transition layer is 5 to 50μ; the thickness of the main layer is 10 to 50μ.

The proposed heterogeneous structure with a composition gradient substantially reduces the harmful effect of the substrate 1 on the crystalline structure and luminescent properties of the main semiconductor layer 3.

This is due to the introduction of the transition layer 2 and the additional layer 7 which provide for a gradual transition from the material of the substrate 1 with its specific crystallographic properties to the material of the main semiconductor layer 3 whose properties are somewhat different.

This accounts for a perfect crystalline structure of the main semiconductor layer 3 and ensures a high quality of semiconductor instruments with working elements manufactured on the basis of the proposed heterogeneous structure with a composition gradient.

Heterogeneous structures in accordance with the present invention possess good morphological surface properties and are marked by low internal mechanical stresses.

Shearing of such a heterostructure at a perpendicular to its surface, which structure is epitaxially grown on the substrate 1 with the surface orientation (100), yields high-quality optical resonator mirrors along the main axis 4 whose direction may be selected to coincide with the crystallographic direction [110].

The use of such a heterogeneous structure as a working element improves the radiation characteristics of the laser: it reduces the threshold current density required to excite laser generation and raises the efficiency of converting the excitation energy into the luminous energy of the laser.

The gradual transition from the material of the substrate 1 to the material of the main semiconductor layer 3 makes it possible to use a considerably broader range of semiconductor compounds to produce the main semiconductor layer 3.

It is now possible to select the components of the main layer 3 from different classes of semiconductor materials and thus produce a series of heterostructures for working elements of lasers and photodectors which can operate within a wide range of wavelengths, from the near ultraviolet region to the infrared region.

For example, a heterogeneous structure with the main semiconductor layer of $CdS_xSe_{1-x}$ ensures laser radiation and photoreception in the range of wavelengths of 0.5 to 0.7 mu.

A working element of a semiconductor instrument on the basis of a heterogeneous structure with the main layer of $GaAs_xP_{1-x}$ provides for radiation and photoreception in the range of 0.65 to 0.9μ.

If a structure is produced on the basis of the main layer 3 of $InAs_xP_{1-x}$, the wavelengths of radiation are between 0.9 and 3μ; if the main layer of a heterogeneous structure with a composition gradient is of solid solution of $PbS_xSe_{1-x}$, the range of wavelengths is 4 to 8μ.

Finally, the range of radiated and received wavelengths may be 6 to 45μ if the working element of laser and photoreception instruments is based on a heterogeneous semiconductor structure of the proposed type with the main semiconductor layer 3 of $Pb_xSn_{1-x}Te$.

In addition, in each of the above-mentioned structures, there can be ensured a continuous and gradual change in the composition along the main axis 4 of the layer 3; x may change along said axis 4 either linearly or in accordance with any other law.

This makes it possible to uniformly adjust generation wavelengths of a laser within a broadrange.

In the proposed heterogeneous structure the composition gradient has a constant direction over the entire area of the main semiconductor layer 3 (along the main axis 4); this makes it possible to produce a working element of a laser having resonators (mirror layers) on the side faces of the main semiconductor layer 3.

These mirror layers can be produced by shearing parts of the structure at a perpendicular to the surface of the main semiconductor layer 3 grown on a substrate with a crystallographic orientation of the surface (100).

The use of such side resonators raises the radiated power of a laser, the radiation being directed at a perpendicular to said sheared side faces.

Another advantage of the proposed heterogeneous structure resides in the fact that the law of change in the concentration of doping impurities is independent of the law of change in the composition of the main layer 3, which makes it possible to achieve a constant doping level both along the main axis 4 and along the Z axis and thus ensure a constant radiated power over the entire range of wavelengths.

According to the invention, the method for producing the proposed heterogeneous semiconductor structure with a composition gradient is as follows.

The process consists in chemically transferring a semiconductor compound through the gaseous phase onto the surface of the substrate 1.

Figure 4:
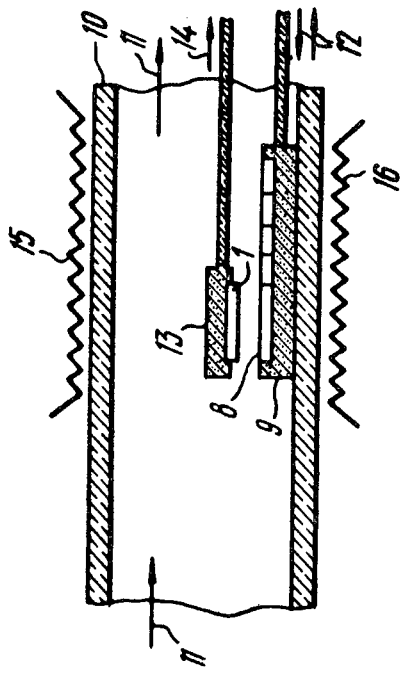
FIG. 4 is a view of a plant for carrying out the proposed method for producing the heterogeneous structure in accordance with the invention.

A solid source 8 (FIG. 4) comprising two components, AB and AC, and a doping impurity is placed in a source container 9 which is a body having a recess for the material of the source 8. The container 9 must be made from a material which possesses good thermal conduction, but does not react with the semiconductor material and the chemical carrier.

Graphite is a good material for the container 9.

The container 9 of the source 8 is placed in a reactor which is a tube 10 through which there is continuously passed a flow of gas with the chemical carrier, which flow is directed as shown by the arrow 11.

The gas may be hydrogen, argon, and helium; the chemical carrier may be $I_2$, $Br_2$, HI, HBr, HCl, $H_2O$, and $H_2$.

The container 9 is coupled to a means to ensure progressive motion of said container 9 in the directions shown by the arrows 12.

The substrate 1 is rigidly secured at a distance of 100μ to 1 mm from the surface of the source 8. The substrate 1 is placed in a substrate container 13 which is provided with means for moving said container 13 in the direction shown by the arrow 14.

The container 9 of the source 8 and the container 13 of the substrate 1 are arranged in the tube 10 and adapted for movement relative to each other so that the distance between the surface of the source 8 and that of the substrate 1 is always constant.

Said distance is selected to be between 100μ and 1 mm.

Prior to the start of the process, the substrate container 13 is heated by a heater 15 to a temperature $T_1$ which is above 450° C.

Warming up the substrate 1 to a temperature below 450° C. is impracticable, because low mobility of atoms, which are deposited in the course of epitaxial growth on the surface of the substrate 1, accounts for defects of the heterogeneous structure being produced.

The container 9 of the souce 8 is heated by a heater 16 to a temperature $T_2$ which is above 620° C.

As a result, there is a difference in the temperatures of the source 8 and the substrate 1.

The temperature of the heaters 15 and 16 is raised until reaching the respective temperatures $T_1$ and $T_2$.

The difference of the temperatures $T_1$ and $T_2$ is the moving force of the physico-chemical process of transferring a semiconductor compound through the gas phase from the source 8 to the substrate 1.

The temperatures $T_1$ and $T_2$ are selected from the range of temperatures between 600° C. and 1,200° C., depending upon the compounds of the source 8, the material of the substrate 1 and the nature of the chemical carrier.

Upon reaching the specified temperatures $T_1$ and $T_2$, there is directed into the tube 10 a gas flow with a chemical carrier; the container 9 of the source 8 starts gradually moving closer to the container 13 of the substrate 1.

The length of the source 8 (FIG. 5) with a specified rate of change in its composition corresponds to the length of the substrate 1 along the main axis 4. The source 8 is composed of several adjacent strips 17 which extend in parallel with the edges of said source 8.

Each of the strips 17 has a constant ratio of its own between the AB and AC components.

The width of each strip 17 is less than or equal to the doubled distance between the surface of the source 8 and the surface of the substrate 1.

The first strip 17, which is at the first edge of the source 8, has a maximum content of the AB component; the last strip 17, which is at the second edge of the source 8, has a maximum content of the AC component.

The ratios of the AB and AC components in two adjacent strips 17 differ by a value corresponding to the quotient of the division of the required value of the composition gradient of the main semiconductor layer 3 (FIG. 2) by the width of said two adjacent strips 17 (FIG. 5).

The source 8 may be composed of strips 17 of a powder blend.

According to an alternative embodiment, the source 8 is composed of monolithic solid plates (strips 17) of solid solutions, each plate having its own ratio between the AB and AC components.

The source 8 (FIG. 6) may have an additional strip 18 which is adjacent to the first of the strips 17 and has a composition with a maximum content of the AB compound.

The width of the strip 18 must be at least equal to the length of the substrate 1 along the main axis 4.

Figure 2:
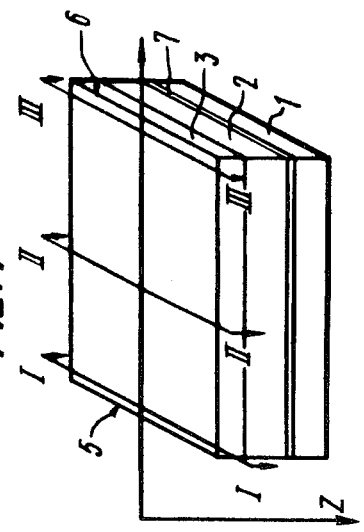
FIG. 2 is a schematic view of an alternative embodiment of the heterogeneous structure with a composition gradient in accordance with the invention.

Each strip 17 of the source 8 shown in FIGS. 5 and 6 has a doping impurity, the percentage of said impurity being determined by the required doping level of the main semiconductor layer 3 (FIG. 2).

As soon as the strip 18 (FIG. 6) of the source 8 with a maximum content of the AB component of the solid solution is at the required distance from the substrate 1, there takes place a transfer of the material of the source 8 and crystallization of this material on the cooler substrate 1, which results in the formation of the additional layer 7 1 to 5$\mu$ thick.

The strip 18 of the source 8, which only comprises the AB component, is left to stay under the substrate 1 for 5 to 10 minutes, i.e. for a period of time required for the formation of the layer 7.

As the layer 7 has been grown, the source 8 is set in progressive motion, so that all the strips 17 of said source 8 are successively brought to the substrate 1.

The source 8 moves along the main axis 4, in parallel with the surface of the substrate 1, at a speed of 100 to 0.1 cm per hour, depending upon the required thickness of the transition layer 2 of the heterogeneous structure (FIG. 7) that is being grown during this period.

As a result, there takes place a transfer of the material of each next strip 17 of the source 8 to the portion of the surface of the substrate 1, which has been already coated with the additional layer 7 (FIG. 2), which portion is the closest to the given strip 17 (FIG. 5) of the source 8 at the given instant. The material is deposited on the substrate 1 to form a strip whose shape is similar to the shape of the given first strip 17 of the source 8.

In the course of the progressive motion of the source 8, the deposition strip moves accordingly from the first strip 17 of the source over the surface of the additional layer 2.

Simultaneously, the deposition strip of the next, second strip 17 of the source 8 moves after the first deposition strip, and the material being deposited again coats the solid solution layer deposited on the first strip 17 of the source 8.

The process is repeated a number of times corresponding to the number of the strips 17 of the source 8; the result is the formation of the transition semiconductor layer 2 of the heterogeneous structure, the composition of said layer 2 changing from the composition, whose crystallographic properties are the closest to those of the material of the substrate 1, to the composition corresponding to that of the main semiconductor layer 3 of the heterogeneous structure.

The time of growing the transition semiconductor layer 2 must be sufficient to ensure a thickness of the layer 2 which is enough to considerably reduce the mechanical stresses due to differences in the crystallographic parameters of the substrate 1 and the main layer 3 of the heterogeneous structure.

Each 0.1 percent of said difference is to be compensated by no less than 1$\mu$ of the thickness of the transition layer 2.

Hence, in growing the main layer 3 of solid solution of $GaAs_{0.5}P_{0.5}$, whose lattice constant differs by 2.5 percent from that of GaAs which is the material of the substrate 1, the thickness of the transition layer 2 must be no less than 25$\mu$.

With normal rates of the chemical transfer of a material through the gas phase, which provide for the epitaxial growth at a rate of 25 to 50$\mu$ per hour, it takes 30 to 60 minutes to form the main working layer 3 of the heterogeneous structure.

The epitaxial growth of the main layer 3 is carried out from the stationary source 8 when its strips 17 are all brought under the substrate 1, as shown in FIG. 7. As shown in FIG. 7, the additional layer 7 and the transition layer 2 have already been grown.

The source 8 remains in this position for 1 to 10 hours, depending upon the required thickness of the layer 3.

The process of growing the main semiconductor layer 3 of the heterogeneous structure with a composition gradient comprises simultaneous processes of transferring the material from each strip 17 of the source 8 to the nearest portion of the surface of the newly formed transition layer 2.

The main layer 3 is composed of a series of parallel deposition strips corresponding to the successively arranged strips 17 of the source 8.

The average chemical composition of each deposition strip is close to the composition of the corresponding strip 17 of the source 8; however, in the course of the transfer through the gas phase, there takes place partial diffusion mixing of the materials of the adjacent strips 17, which leave the source 8 to enter the gaseous phase.

The result is the smooth and gradual change in the composition of solid solution in the main layer 3 of the heterogeneous semiconductor structure.

Side diffusion in the gas phase from each strip 17 of the source 8 effectively proceeds at a distance which is not greater than the distance between the surfaces of the substrate 1 and the source 8; hence, the width of each strip 17 of the source 8 is not greater than the doubled gap between the surfaces of the substrate 1 and the source 8.

If the gap between the source 8 and substrate 1 is 1 mm, the maximum width of each strip 17 of the source 8, at which there yet takes place a smooth change in the composition of the solid solution in the main layer 3, is 2 mm.

If the strips 17 of the source 8 are wider, the change in the composition of the solid solution of the main layer 3 will be stepwise.

Therefore, it is undesirable that the epitaxial growth of the heterogeneous structure with a composition gradient should be carried out with a gap between the surfaces of the substrate 1 and source 8 less than 200$\mu$; otherwise, the source 8 must be composed of a very great number of thin (up to 400$\mu$) strips 17.

It is extremely difficult to provide such a source 8; moreover, it is difficult to ensure the correct geometrical shape of each strip 17.

On the other hand, large gaps (of more than 1 mm) make it necessary that the strips 17 of the source 8 should be wide (about 2 mm).

The number of the strips 17 is normally limited by the overall length of the substrate 1 along the main axis 4, which length is normally 10 to 50 mm; this, in turn, limits the possibility of accurately controlling the composition gradient of the main semiconductor layer 3 of the heterogeneous structure.

Besides, gaps of more than 1 mm add the convection mixing of the gaseous medium to the diffusion process, which results in uncontrollable and unreproducible deviations of the composition of the main layer 3 from predetermined values and impairs the parameters of instruments produced on the basis of heterogeneous structures with such deviations.

The transfer of the AB and AC components is accompanied by the chemical transfer of the doping impurity found in each strip 17 of the source 8.

The impurity content in the strips 17 is determined by the required doping degree of the main layer 3 and is meant to ensure normal functioning of semiconductor instruments, wherein the heterogeneous structure being produced is going to be used as the working element.

Normal operation of a semiconductor laser requires a sufficiently great number of electron states in the semiconductor crystal, so the doping is carried out to bring about degeneracy of the semiconductor.

This limit depends upon the nature of the semiconductor material; for example, for wide-range semiconductors it amounts to $10^{18}$ to $10^{19}$ cm$^{-3}$.

It is desirable that the doping level be variable along the main axis 4 of the layer 3, depending upon the composition gradient value of the solid solution in said layer 3.

In some cases, it is sufficient to ensure strong doping with uniform distribution of the doping impurity along the main axis 4.

If the doping impurity is transferred from the source 8 to the layer 3 being grown absolutely without any losses, the doping level of the source 8 must be identical with the desired doping level of the main layer 3 of the heterogeneous structure with the composition gradient.

The proposed method for producing a heterogeneous structure with a composition gradient is advantageous in many respects.

Firstly, the method ensures a broad range of a continuous change in the composition of solid solution of the layer 3 along the main axis 4, which may amount to several tens of mole percent.

Secondly, the method ensures a wide range of controlled composition gradient values along the main axis 4, i.e. of 5 to 40 mole percent per centimeter.

Thirdly, the proposed method ensures a high accuracy of maintaining a preset composition gradient over the surface of the heterogeneous structure, as well as the rectilinearity of the constant composition lines on the surface of the heterogeneous structure.

In the fourth place, the proposed method is advantageous in that it makes it possible to control the structure's composition both over its surface (along the axis 4) and through its thickness; the method also makes it possible to control the rate of change in doping impurities.

In the fifth place, the method of the present invention ensures a high output and produces, without any preliminary heat treatment, a heterogeneous structure with a composition gradient, which can be used as the working element of a laser.

The proposed method is carried out with the aid of a simple, but highly effective source which ensures the production of heterostructures with a predetermined composition gradient and required useful properties.

The advantages of the present invention will be more readily understood from the following examples of specific heterogeneous semiconductor structures with composition gradients, as well as of techniques and sources employed to produce such structures.

EXAMPLE 1

The substrate 1 (FIG. 8) is a monocrystalline rectangular plate of GaAs having a length of 20 mm, a width of 10 mm, and a thickness of 400μ. The orientation of the surface of the substrate of GaAs is (111) B.

The source 8 (FIG. 9) is composed of eight strips 17 filled with a powder-like blend which is a mixture of GaP and GaAs. Each strip 17 is 2 mm wide.

In addition, there is a strip 18 of GaAs, which is 20 mm long.

The first strip 17, which is adjacent to the strip 18, wholly consists of GaAs. The next strip 17 comprises 6 mole percent GaP and 94 mole percent GaAs. The next strip 17 comprises 12 mole percent GaP and 88 mole percent GaAs, etc. The last, eighth strip 17 comprises 42 mole percent GaP and 58 mole percent GaAs. The blend is doped with tellurium to a concentration of free electrons of $2\cdot10^{18}$ cm$^{-3}$.

The epitaxial growth of the given heterogeneous structure of GaAs$_{1-x}$P$_x$ is carried out with the use of the chemical transfer reaction involving steam (H$_2$O) and a flow of H$_2$. The partial steam pressure is 5 mm of mercury.

The temperature of the substrate 1 (FIG. 6) is selected to be 900° to 950° C.; the temperature of the source 8 is selected to be between 970° and 1,010° C.

The gap between the surfaces of the substrate 1 and the source 8 is 400 to 700μ.

The strip 18 of the source 8 is moved along the substrate 1 during 30 minutes at a speed of 40 mm per hour, which results in the formation of the additional layer 7 of a wedge-like shape.

The source 8 is then moved for 20 minutes at a speed of 60 mm per hour to form the transition layer 2 (FIG. 7), after which the source 8 is stopped. At this point, there starts the growth of the main semiconductor layer 3 with a composition gradient, which is carried out for two and a half hours.

Figure 8:
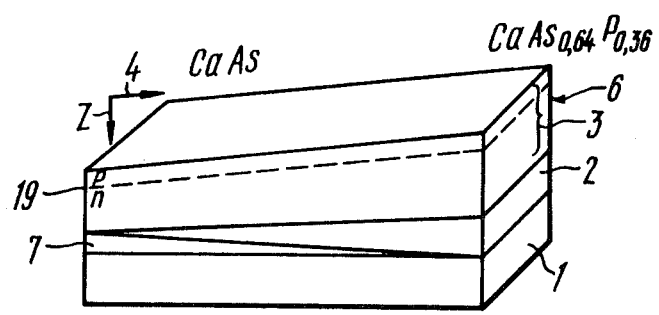
FIG. 8 is a view of a heterogeneous semiconductor structure for lasers with a composition gradient on the basis of a solid solution of $GaP_xAs_{1-x}$ in accordance with the invention.

The heterogeneous structure thus produced is shown in FIG. 8.

The additional semiconductor layer 2 of the structure consists of GaAs and has a variable thickness from 0 near the edge 6 of the heterogeneous structure to 12μ near the edge 5.

The transition layer 2 is solid solution whose composition changes, thickness-wise, from GaAs near the boundary between the layers 7 and 2 to the composition of the main layer 3 on the boundary between the layers 2 and 3. The thickness of the layer 2 is also variable, the maximum thickness being 21μ near the edge 6 of the structure. As is seen from the drawing, the additional layer 7 serves to compensate the wedge-like shape of the transition layer 2.

The main semiconductor layer 3 is solid solution of GaP$_x$As$_{1-x}$ whose composition changes gradually and continuously from the edge 5 containing GaAs to the edge 6 consisting of GaAs$_{0.64}$P$_{0.36}$; x linearly changes along the axis 4 over the length of 20 mm within these limits: $0 \leq x \leq 0.36$.

The layer 3 has a variable thickness along the axis 4, which is due to different growth rates of the solid solution of GaP$_x$As$_{1-x}$ with different values of x.

The composition of the transition layer 2 near the edge 6 of the structure changes gradually and continuously, thickness-wise, from GaAs to GaAs$_{0.64}$P$_{0.36}$.

The value of the composition gradient over the thickness of the layer 2 near the edge 6 amounts to 1.71 mole percent/$\mu$.

The value of the composition gradient of the main layer 3 over the length along the axis 4 amounts to 20 mole percent/cm.

The forbidden gap width of the solid semiconductor solution of GaAs$_{1-x}$P$_x$ changes from 1.4 eV to 1.8 eV.

The structure is doped with tellurium and has a concentration of free electrons from $8 \cdot 10^{17}$ to $1 \cdot 10^{18}$ cm$^{-3}$.

The heterogeneous structure thus produced has a smooth surface which is free of pyramids of growth. The dislocation density is $8 \cdot 10^4$ to $6 \cdot 10^5$ cm$^{-2}$ and increases towards the edge 6 of the structure which is rich in P.

Although the lattice parameters of the initial components, GaAs and GaP, differ considerably ($a_{GaAs}=5.654$ Å, and $a_{GaP}=5.450$ Å), the epitaxial growth produces a structure possessing a wide range of composition variations.

The working element of a laser, produced on the basis of this heterogeneous structure, has a broad range of readjustment of radiation wavelengths (over 1,500 Å).

The heterogeneous semiconductor structure with a composition gradient on the basis of GaAs$_{1-x}$P$_x$ and doped with tellurium can be used in electron-beam-pumped lasers.

In order to use this structure as the working element of an injection laser or in a selective spectrometer, it is necessary to provide a p-n junction in the main layer 3.

Such a p-n junction 19 can be produced by using the known technique of diffusion in zinc vapors from the surface of the main layer 3 at a temperature of 800° to 850° C. to a depth of 2 to 20$\mu$.

The depth of the p-n junction 19 is selected within the above limits and is determined by the purpose of the structure being produced.

EXAMPLE 2

The substrate 1 (FIG. 2) is of GaAs with the orientation (111) and is doped with tellurium to a concentration of carriers of $5 \cdot 10^{17}$ cm$^{-3}$. The substrate 1 of GaAs is 20 mm long, 1.5 cm wide, and has a thickness of 300$\mu$.

The source 8 (FIG. 6) comprises eleven strips, including one additional strip 18 and ten strips 17.

The strip 18 consists of a powdered mixture of grains of InAs and InP, the ratio being 50 mole percent InAs and 50 mole percent InP. In the next ten strips 17 the composition changes by 5 mole percent from strip to strip.

Thus, the first strip 17 has 55 mole percent InAs and 45 mole percent InP; the second strip 17 consists of 60 mole percent InAs and 40 mole percent InP, etc.; the last strip 17 consists of 100 mole percent InAs.

The strip 18 is 20 mm wide; each of the strips 17 is 2 mm wide. The semiconductor material of the strips 17 and 18 is doped with tellurium.

The epitaxial growth is carried out by a chemical transfer of the material of the source 8 onto the substrate 1, which transfer takes place in the gaseous phase comprising a mixture of H$_2$ and one pecent by volume HCl.

The temperature of the source 8 is 700° C., while that of the substrate 1 is 680° C. The spacing between the surfaces of the source 8 and substrate 1 is 600$\mu$.

The additional layer 7 (FIG. 6) is grown during 20 minutes at a growth rate of 15$\mu$ per hour.

The transition layer 2 (FIG. 7) of the heterogeneous structure is grown during 5 hours with the strips 17 moving in relation to the substrate 1 at a speed of 4 mm per hour.

The growth rate of the transition layer 2 is 15$\mu$ per hour.

The epitaxial growth of the main layer 3 of the structure is carried out after the strips 17 of the source 8 stop under the substrate 1.

The duration of the growth of the layer 3 is 3 hours.

The layer 3 is doped in the course of the growth by a transfer of the doping impurity, i.e. tellurium, from the source 8 into the layer 3. The tellurium transfer takes place without any losses, so in order to dope the main layer 3 to reach a concentration of electrons of $1 \cdot 10^{18}$ cm$^{-3}$, which is necessary to produce a high-quality electron-excited laser, use should be made of a powdered semiconductor material of the source 8, which material is doped with tellurium to the same concentration of electrons.

The result of the above operations is a heterogeneous structure of InAs$_{1-x}$P$_x$ with a composition gradient.

The lattice parameter of the substrate 1 (FIG. 2), s=5.6535 Å; the substrate 1 is 300$\mu$ thick, 2 cm long and 1.5 cm wide.

The additional semiconductor layer 7 comprises a solid solution of InAs$_{0.5}$P$_{0.5}$ and is 5$\mu$ thick.

The transition semiconductor layer 2 is also of a solid solution whose composition varies over its thickness from InAs$_{0.5}$P$_{0.5}$ near the boundary between the surfaces of the layers 2 and 7 to the composition of the main layer 3 near the boundary between the surfaces of the layers 3 and 7.

The main semiconductor layer 3 is solid solution of InAs$_{1-x}$P$_x$, where x changes along the axis 4 within $0.05 \leq x \leq \leq 0.5$ mole unit.

Near the edge 5 of the heterogeneous structure, the layer 3 consists of InAs$_{0.5}$P$_{0.5}$; the lattice parameter a=5.963 Å. Close to the edge 6, the composition of the layer 3 corresponds to this formula:

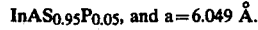

InAs$_{0.95}$P$_{0.05}$, and a=6.049 Å.

Near the edge 6 of the heterogeneous structure, the composition of the transition layer 2 changes in thickness from InAs$_{0.5}$P$_{0.5}$ to InAs$_{0.95}$P$_{0.05}$. The thickness of the transition layer 2 is 70$\mu$.

The selection of the thickness of the layer 2 is based on the premise that the lattice parameter of the substrate 1 of GaAs is: $a_{GaAs}=5.654$ Å; the lattice parameter of InAs, $a_{InAs}=6.058$ Å; and the lattice parameter of InAs$_{0.5}$P$_{0.5}$, $a_{InAs0.5P0.5}=5.963$ Å.

Hence, the greatest difference in the lattice parameters of the substrate 1 and the main layer 3 is observed in that portion of the layer 3, where the composition is the closest to InAs.

In this case, the relative difference of parameters amounts to:

$(a_{InAs} - a_{GaAs}/a_{GaAs}) \cdot 100\% = 7\%$.

In order to avoid excessive mechanical stresses, the composition of the heterogeneous structure must be changed so that the value of the gradient of the change in the lattice parameter in the transition layer 2 should not be in excess of 0.1 %/$\mu$.

Hence, with a difference in the lattice parameters of 7%, the thickness of the transition layer 2 must be no less than 70$\mu$.

The main layer 3 is 45$\mu$ thick. The layer 3 is doped with tellurium to a concentration of free electrons of $1 \cdot 10^{18}$ cm$^{-3}$.

The composition gradient of the main layer 3 is 22.5 mole %/cm.

The fact that InAs$_{0.95}$P$_{0.05}$ is produced instead of InAs, as it should be in the case of the last strip 17 (FIG. 6) of the source 8, is due to the diffusion of the components through the gaseous phase in the gap between the source 8 and substrate 1.

The forbidden gap width changes from one edge of the structure to the other by 0.8 eV, i.e. from 0.42 eV for InAs $_{0.95}$P$_{0.05}$ to 0.82 eV for InAs$_{0.5}$P$_{0.5}$.

The semiconductor material of the main layer 3 (FIG. 2) is a solid solution of InAs$_{1-x}$P$_x$ and has an energy-band structure with forward-biased junctions.

The change in the width of the forbidden gap from 0.42 to 0.82 eV ensures readjustment of the generation wavelengths of a laser produced on the basis of this heterogeneous structure within the limits of 1.5 to 2.8$\mu$.

EXAMPLE 3

The substrate 1 (FIG. 2) is of gallium arsenide GaAs with the orientation (100)±5' and is shaped as a rectangular plate. The dimensions of said plate are 15 mm along the axis 4 and 25 mm at a perpendicular to said axis 4. The substrate 1 is 300$\mu$ thick.

The source 8 (FIG. 6) is composed of eleven strips. The additional strip 18 is a plate of InP which is 30 mm wide. The strips 17 are recesses in the unit 9 of the source 8, filled with powdered mixtures of InP and InAs of solid solution. Besides, all the strips 17 contain a doping impurity which is tellurium, its concentration being $2 \cdot 10^{18}$ cm$^{-3}$.

The composition of the first strip 17 may be conventionally designated as InAs$_{0.05}$P$_{0.95}$; said strip 17 is 5 mm wide.

Composition of the second strip 17: InAs$_{0.1}$P$_{0.9}$; width, 2 mm.

Composition of the third strip 17: InAs$_{0.15}$P$_{0.85}$; width, 2 mm.

Composition of the fourth strip 17: InAs$_{0.2}$P$_{0.8}$; width, 2mm.

Composition of the fifth strip 17: InAs$_{0.25}$P$_{0.75}$; width, 2 mm.

Composition of the sixth strip 17: InAs$_{0.3}$P$_{0.7}$; width, 2 mm.

Composition of the seventh strip 17: InAs$_{0.35}$P$_{0.65}$; width, 2 mm.

Composition of the eighth strip 17: InAs$_{0.4}$P$_{0.6}$; width, 2 mm.

Composition of the ninth strip 17: InAs$_{0.45}$P$_{0.55}$; width, 2 mm.

Composition of the tenth strip 17; InAs$_{0.5}$P$_{0.5}$; width, 5 mm.

The epitaxial growth is carried out by chemical transfer of the material of the source 8 (FIG. 4) onto the substrate 1, the transfer taking place in the gaseous phase which is a mixture of H$_2$ and one percent by volume HCl.

The temperature of the source 8 is maintained about 720° C.; the temperature of the substrate 1 is maintained about 700° C.

The gap between the surfaces of the source 8 and substrate 1 is 1 mm.

The additional layer 7 (FIG. 6) is grown during 12 minutes; after the formation of the additional layer 7, the source 8 moves in relation to the substrate 1 for 4 hours at a speed of 5 mm per hour.

After the growing of the transition layer 2 (FIG. 7) has been completed, the source 8 is stopped, and there starts the formation of the main semiconductor layer 3, which is carried out during 2 hours.

The result is a heterogeneous semiconductor structure of InAs$_{1-x}$P$_x$ with a composition gradient, which structure is doped with tellurium from the source 8 to a concentration of electrons of $2 \cdot 10^{18}$ cm$^{-3}$.

By shearing the large sample, which is shaped as a rectangular plate, one obtains a sample shaped as a narrow bar which is 1.5 cm long and 0.5 mm wide.

The lattice parameter of the substrate 1 (FIG. 2), a=5.6535 Å; the thickness of the substrate 1 is 300$\mu$.

the additional semiconductor layer 7 is of solid solution of InP, its thickness being equal to 3$\mu$.

The transition semiconductor layer 2 is a solid solution whose composition changes over its thickness from InP near the boundary between the surfaces of the layers 2 and 7 to the composition of the main layer 3 near the boundary between the surfaces of the layers 3 and 7.

The main semiconductor layer 3 is of solid solution of InAs$_{1-x}$P$_x$, whose x designates molar fractions of the components of the solid solution and changes along the axis 4 within these limits: $0.5 \leq x \leq 1$.

Near the edge 5 of the heterogeneous structure, the layer 3 consists of InP with a=5.8688 Å; near the edge 6 of the structure, the composition of the layer 3 corresponds to the formula InAs$_{0.5}$P$_{0.5}$; in this portion, a=5.963 Å.

Near the edge 6 of the heterogeneous structure, the composition of the transition layer 2 changes thickness-wise from InP to InAs$_{0.5}$P$_{0.5}$.

The greatest difference in the lattice parameters of the layer 3 with the composition gradient and the substrate 1 of gallium arsenide is:

(5.9663 Å − 5.6535 Å/5.6535 Å)·100% =5.2%.

The thickness of the transition layer 2 is 60$\mu$.

The thickness of the main layer 3 with the composition gradient is 30$\mu$; the value of the composition gradient along the main axis 4 is determined as follows:

(50 mole %/1.5 cm)=(33 mole %/cm).

The structure is doped with tellurium, which doping impurity is transferred from the source 8 (FIG. 4) in the course of the epitaxial growth. The concentration of the charge carriers in the main layer 3 (FIG. 2) of the heterogeneous structure is $2 \cdot 10^{18}$ cm$^{-3}$, because the tellurium is transferred in the ratio of 1:1, i.e. without any losses.

The change in the composition of the main layer 3 from InP to InAs$_{0.5}$P$_{0.5}$ makes it possible to smoothly and continuously adjust the wavelength of a laser employing a working element on the basis of the foregoing structure within the range of 0.9 to 1.5μ.

EXAMPLE 4

The substrate 1 (FIG. 2) is a monocrystalline rectangular plate of ZnTe. The plate is 0.4 mm thick, 1 cm wide and 3 cm long; the orientation is (111).

The source 8 (FIG. 6) is composed to thirty strips 17; each strip 17 is 1 mm wide and is of a mixture of powdered CdS and CdSe with a grain size of 0.1 to 0.15 mm. There is also an additional strip 18 of CdSe, which is 35 mm wide.

The composition of the strips[17] is discretely changed from strip to strip from the composition of the first strip 17, which is designated as CdSe, to the composition of the last strip 17.

The epitaxial growth (FIG. 4) of the layers of the heterogeneous semiconductor structure of $CdS_xSe_{1-x}$ is carried out by the chemical transfer of the material of the source 8 onto the substrate 1, the transfer taking place in the gaseous phase comprising $H_2$ purified by diffusion through a diaphragm of palladium. Hydrogen in this case is the carrier, whereto there is added HCl in an amount of 0.1 to 0.5 volume percent.

The temperature of the source 8 is 730° C.; the temperature of the substrate 1 is 650° C.

The gap between the surfaces of the source 8 and substrate 1 is 0.6 mm.

The additional layer 7 (FIG. 6) is formed during 2 hours; after the formation of said layer 7 has been completed, the source 8 is set in motion relative to the substrate 1 for 13 hours at a speed of 2.5 mm per hour.

This results (FIG. 7) in the formation of the semiconductor layer 2, after which the source 8 is stopped and left under the substrate 1 for 10 hours, during which period there is grown the main layer 3 of the heterogeneous structure.

It takes 25 hours to form the entire heterogeneous semiconductor structure with a composition gradient of solid solution of $CdS_xSe_{1-x}$.

The sample thus produced is 30 mm long and 10 mm wide; the thickness of the substrate 1 (FIG. 2) is 0.4 mm.

The additional semiconductor layer 7 consists of CdSe and is 6μ thick.

The transition semiconductor layer 2 is of solid solution whose composition changes thickness-wise from CdSe near the boundary between the layers 2 and 7 to the composition of the main layer 3 near the boundary between the layers 3 and 7. The layer 2 is 40μ thick.

The main semiconductor layer 3 is of solid solution of $CdS_xSe_{1-x}$. The composition of the layer 3 changes gradually and continuously along the axis 4 from $CdS_{0.01}Se_{0.99}$ near the edge 5 of the heterogeneous structure to $CdS_{0.98}Se_{0.02}$ near the edge 6 of the heterogeneous structure.

X designates molar fractions of the components of the solid solution and changes along the axis 4 within these limits: $0.01 \leq x \leq 0.98$.

The composition of the transition layer 2 changes thickness-wise near the edge 6 of the heterogeneous structure from CdSe to $CdS_{0.98}Se_{0.02}$.

The thickness of the main layer 3 is 30μ; the value of the composition gradient is 3.2 mole percent/cm.

The layer 3 is doped with chlorine to a concentration of electrons of $2 \cdot 10^{18}$ cm$^{-3}$, the doping being carried out during the stage of forming the main layer 3 by adding gaseous HCl to hydrogen.

In the heterogeneous semiconductor structure, with a composition gradient of solid solution of $CdS_xSe_{1-x}$ thus produced, the width of the forbidden gap changes smoothly and continuously from 1.9 to 2.4 eV, which makes it possible to readjust the wavelength of a laser from 0.5 to 0.7μ.

EXAMPLE 5

The substrate 1 is a monocrystalline rectangular plate of PbTe which is 20 mm long. The plate is cut out of a monocrystalline ingot of PbTe grown by using Bridgeman's method and is annealed in vacuum at a temperature of 400° C.

The source 8 (FIG. 6) is composed of eleven strips 17 filled with a powdered blend which is a mixture of SnTe and PbTe with lattice parameters $a_{SnTe}=6.32$ Å and $a_{PbTe}=6.45$ Å. There is also a strip 18 which is 30 mm wide. The width of each of the strips 17 is 2 mm.

The first strip 17, which is adjacent to the strip 18, wholly consists of PbTe; the next strip 17 comprises 6 mole percent SnTe and 94 mole percent PbTe, etc.

The last strip 17 comprises 60 mole percent SnTe and 40 mole percent PbTe.

The material of the source 8 is doped with Bi to a concentration of free electrons of $10^{19}$ cm$^{-3}$.

The epitaxial growth of this heterogeneous structure of $Pb_{1-x}Sn_xTe$ is carried out by chemical transfer with the use of the transporation reaction in iodine at a pressure of 1 atm.

The temperature of the source 8 (FIG. 4) is selected to be from 700 to 780° C.; the temperature of the substrate 1 is between 600° and 700° C.

The gap between the source 8 and substrate 1 is 500μ.

The epitaxial growth is preceded by some preparatory operations. The reactor 10 is purged with argon; the soruce 8 and substrate 1 are heated to the above-mentioned temperatures; iodine vapors are directed to the tube 10. The epitaxial growth rate is 15 to 60μ per hour, depending upon the specific temperature selected within the foregoing range of temperatures.

The strip 18 of the source 8 (FIG. 6) is then brought under the substrate 1, and the additional layer 7 is formed during 5 to 20 minutes, depending upon the specific temperature at which the chemical transfer is carried out.

Then the source 8 (FIG. 7) starts moving in relation to the substrate 1 at a speed of 0.3 mm/min during 0.5 to 2 hours to form the transition layer 2 of the heterogeneous structure.

The source 8 is then stopped and left for 1 to 3 hours under the substrate 1 for the formation of the main semiconductor layer 3.

After the process of epitaxially growing the heterogeneous structure is ended, the tube 10 is again purged with an inert gas and cooled, whereupon the finished heterogeneous structure of $Pb_{1-x}Sn_xTe$ is removed therefrom.

The length of the heterogeneous structure sample thus produced is 20 mm; the thickness of the substrate 1 (FIG. 2) is 300μ.

The additional semiconductor layer 7 consists of a solid solution of PbTe and is 5μ thick.

The transition semiconductor layer 2 is a solid solution whose composition changes thickness-wise from PbTe near the boundary between the layers 2 and 7 to the composition of the main layer 3 near the boundary between the layers 2 and 3. The thickness of the layer 2 is 300μ.

The main semiconductor layer 3 is a solid solution of $Pb_{1-x}Sn_xTe$ and has a thickness of 50μ; x designates the molar fractions of the components and linearly changes along the axis 4 over the length of 20 mm within these limits: $0 \leq x \leq 0.6$.

The composition of the layer 3 changes gradually and continuously along the axis 4 from PbTe near the edge 5 to $Pb_{0.4}Sn_{0.6}Te$ near the edge 6 of the heterogeneous structure.

The composition of the transition layer 2 near the edge 6 of the heterogeneous structure changes gradually and continuously from PbTe to $Pb_{0.4}Sn_{0.6}Te$.

The value of the composition gradient of the main layer 3 is 30 mole %/cm.

Doping with bismuth to a concentration of $2-5 \cdot 10^{18}$ cm$^{-3}$ yields an n-type material.

The heterogeneous structure thus produced makes it possible to change x within a broad range, although there is some difference in the lattice parameters of PbTe and SnTe: $a_{PbTe}=6.45$ Å, whereas $a_{SnTe}=6.32$ Å.

The width of the forbidden gap changes from 0.36 eV for PbTe to 0.1 eV for $Pb_{0.4}Sn_{0.6}Te$ (at 77° K.); zero is crossed with x=0.4.

When used as the working element of a laser, this type of structure provides for laser radiation within a range of wavelengths from 6μ near the edge of the layer 3 corresponding to PbTe to 20μ along the line corresponding to $Pb_{0.7}Sn_{0.3}Te$. In addition, with the aid of this structure one can investigate different physical properties of a solid solution of $Pb_{1-x}Sn_xTe$, while gradually moving towards the line corresponding to $Pb_{0.7}Sn_{0.3}Te$, where the width of the forbidden gap is zero.

The heterogeneous semiconductor structure on the basis of the layer 3 of $Pb_{1-x}Sn_xTe$ can also be produced by using the well-known vacuum evaporation technique, because PbTe and SnTe can be sublimited in vacuum ($10^{-5}$ to $10^{-6}$ of mercury) without dissociation in molecules.

The expitaxial growth is carried out at an evaporation temperature of 600° to 800° C.

The source is similar to the source used in the case of the chemical transportation reaction.

The substrate 1 can be made from Ge, $CaF_2$, PbTe, and its temperature is selected to be from 540° to 600° C.

All the stages of producing this heterogeneous structure are similar to those described above. The only difference is that a decrease in the epitaxial growth rate down to 2 to 10μ per hour accounts for a proportional increase in the time during which a structure of a specified thickness is grown.

EXAMPLE 6

The substrate 1 is of GaAs with the orientation (111) As±3'; it is a plate having a size of 10 by 20 mm.

Figure 10:
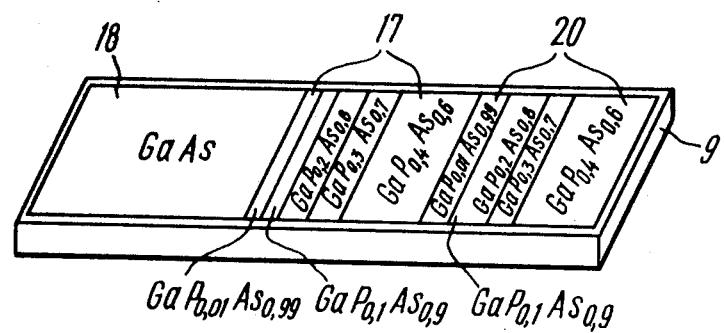
FIG. 10 is a view of a source for producing a heterogeneous semiconductor structure for pressure gauges on the basis of a solid solution of $GaP_xAs_{1-x}$ in accordance with the invention.

The source 8 (FIG. 10) is composed of eleven strips, including one additional strip 18 which is 15 mm wide, five strips 17 and five strips 20.

The strip 18 is of GaAs. The first strip 17 has a composition which is conventionally designated as $GaAs_{0.99}P_{0.01}$ and is 1 mm wide.

The composition of the second strip 17: $GaAs_{0.9}P_{0.1}$; width, 1 mm.

The composition of the third strip 17: $GaAs_{0.8}P_{0.2}$; width, 2 mm.

The composition of the fourth strip 17: $GaAs_{0.7}P_{0.3}$; width, 2 mm.

The composition of the fifth strip 17: $GaAs_{0.6}P_{0.4}$; width, 4 mm.

The composition of the first strip 20: $GaAs_{0.99}P_{0.01}$; width, 2 mm.

The composition of the second strip 20: $GaAs_{0.9}P_{0.1}$; width, 1 mm.

The composition of the third strip 20: $GaAs_{0.8}P_{0.2}$; width, 2 mm.

The composition of the fourth strip 20: $GaAs_{0.7}P_{0.3}$; width, 2 mm.

The composition of the fifth strip 20: $GaAs_{0.6}P_{0.4}$; width, 5 mm.

The first five strips 17 of the source 8 are doped by adding 10 percent by weight metallic iron to the powdered blend.

Said strips 17 are additionally doped with tellurium to a level of $1 \cdot 10^{17}$ cm$^{-3}$.

The strips 20 are doped with tellurium alone to a level of $5 \cdot 10^{17}$ cm$^{-3}$.

The epitaxial growth of the heterogeneous structure with a composition gradient of solid solution of $GaAs_{1-x}P_x$ is carried out by the chemical transfer of the material of the source 8 (FIG. 11) onto the substrate 1. The chemical transfer takes place in the gaseous phase which is a mixture of hydrogen and three volume percent HCl.

The temperature of the structure 1 is 940° C.; the temperature of the source 8 is 960° C.

The gap between the surfaces of the source 8 and substrate 1 is 0.5 mm.

While growing the additional layer 7 (FIG. 6) with a thickness of 5μ, the strip 18 of the source 8 stays for 15 minutes under the substrate 1.

After this, the transition layer 2 (FIG. 7) is formed by further moving the source 8 (i.e. the first through fifth strips 17) under the substrate 1 at a speed of 5 mm per hour.

Figure 11:
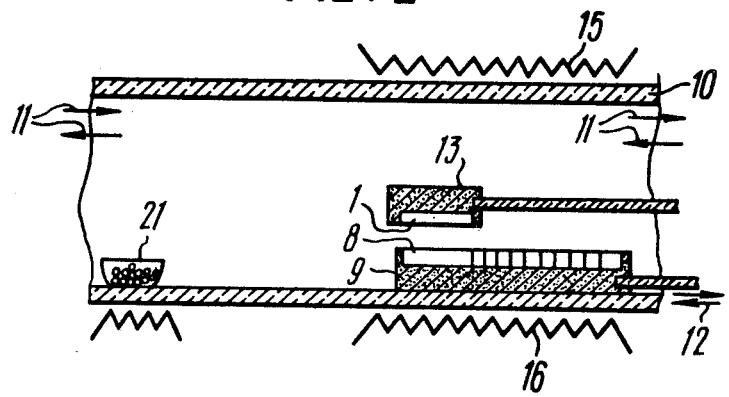
FIG. 11 is a view of a plant for the production of said heterogeneous semiconductor structure for pressure gauges on the basis of a solid solution of $GaP_xAs_{1-x}$ in accordance with the invention.

It takes 2 hours to produce the layer 2 with a thickness of 40μ. In the course of growing the layers 7 and 2, a flow of gas containing iron compounds is directed towards the substrate 1 (FIG. 11). Said iron compounds are produced as a result of the reaction between powdered metallic iron with a grain size of 200μ, heated to a temperature of 850° to 900° C. in a boat pan 21, and HCl contained in the gas flow.

The main layer 3 (FIg. 7) is grown by bringing all the strips 20 (FIG. 10) of the source 8 under the substrate 1 and leaving them there for 30 minutes.

While growing the main layer 3 (FIG. 7), the direction of the gas flow containing iron compounds is reversed in order to avoid the penetration of these compounds into said layer 3.

The main layer 3 is doped with tellurium to a level of $5 \cdot 10^{17}$ cm$^{-3}$ by the transfer of the doping impurity from the strips 20 (FIG. 10) of the source 8 (strips one through five).

Simultaneously, the additional layer 7 (FIG. 7) and the transition layer 2 are doped with an impurity producing deep-lying energy states (iron), as well as an impurity which compensates the uncontrollable acceptor noise (tellurium).

Iron is introduced in the form of powder with a grain size of 100 to 200μ both into all the strips 17 (FIG. 10) of the source 8 and into the gaseous medium.

After the main layer 3 has been produced, the heating is discontinued (FIG. 11), and the tube 10 is purged with an inert gas and cooled, whereupon the finished heterogeneous semiconductor structure is removed therefrom.

Figure 12:
FIG. 12 is a view of said heterogeneous structure on the basis of a solid solution of $GaP_xAs_{1-x}$ to be used as a working element of a pressure gauge, in accordance with the invention.

A structure in the form of a bar of 10 by 0.3 by 0.295 mm (FIG. 12) can be cut from the plate sample grown on the substrate 1, which has a size of 10 by 20 mm.

The heterogeneous semiconductor structure comprises a semi-insulating substrate 1 of i-GaAs with a thickness of 250μ and orientation (111) Ga±3′, an additional semi-insulating layer 7 with a thickness of 5μ, a transition layer 2 of a variable composition on the basis of a semi-insulating solid solution of i-GaAs$_{1-x}$P$_x$ with a maximum thickness of 40μ, and a main layer 3 with a thickness of 10μ, the latter layer being composed of five successively arranged strips of solid solution, respectively comprising GaAs$_{0.99}$P$_{0.01}$, GaAs$_{0.9}$P$_{0.1}$, GaAs$_{0.8}$P$_{0.2}$, GaAs$_{0.7}$P$_{0.3}$, and GaAs$_{0.6}$P$_{0.4}$.

The main layer 3 is doped with tellurium to a concentration of $5 \cdot 10^{17}$ cm$^{-3}$. The electric resistance of the main layer 3 in the direction of the main axis 4 is 200 ohms.

The additional layer 7 and transition layer 2 are simultaneously doped with two impurities producing deep-lying and shallow energy states, (respectively: iron and tellurium), which accounts for high resistivity of said layers 7 and 2 (about $10^4$ ohms per cm).

On the surface of the main layer 3, near the edges 5 and 6, there are applied contacts 22 of an alloy comprising 80% indium and 20% tin, whereto there are connected electrodes 23 of gold wire with a diameter of 70μ. The instrument thus produced is a pressure gauge.

The change in the composition of the main layer 3 proceeds stepwise. A strip 24, whose composition corresponds to $x_1=0.01$, is 1 mm wide; a strip 25 ($x_2=0.1$) is 1 mm wide; a strip 26 ($x_3=0.2$) is 2 mm wide; a strip 27 ($x_4=0.3$) is 2 mm wide; a strip 28 ($x_5=0.4$) is 4 mm wide. The number of the strips (there are five of them) is quite sufficient for practical purposes.

A reduced number of said strips and growing differences in the compositions of the adjacent strips disturb the continuity of the relationship between the sensitivity factor of the pressure gauge and the pressure applied thereto.

An increase in the number of said strips, for example to ten, results in continuous non-linear change in the composition of the solid solution along the main axis 4.

A pressure gauge of this type may have very good characteristics, yet it is extremely difficult to calculate the required smooth change in the strip composition. Such calcuations can only be performed with the aid of a computer, which makes it impractical to produce and employ such gauges for solving specific problems.

An important advantage of the structure described herein above, wherein the main layer 3 comprises portions having different composition and length (1:1:2:2:4) and, consequently, different shares of the total electric resistance of the gauge, resides in reduced dependance of the sensitivity factor upon the pressure, as compared to a structure comprising portions of the same composition, but of equal volumes. The sensitivity factor of a structure with equal volumes of its portions changes from $S_{min}=2.7 \cdot 10^{-5}$ bar$^{-1}$ to $S_{max}$ $7.2 \cdot 10^{-4}$ bar$^{-1}$ (i.e. 28.5 times) in the range of 0 to 40 kilobars. As regards the proposed structure with the ratio between the volumes of its portions of 1:1:2:2:4, the sensitivity factor is more stable and changes in the same range from $S_{min}=2 \cdot 10^{-5}$ bar$^{-1}$ to $S_{max}=5 \cdot 10^{-4}$ bar$^{-1}$, i.e. 25 times.

An extremely important advantage of the proposed heterogeneous structure with a change in the composition along the main axis 4, as compared to the structure produced from uniform solid solution with the intermediary composition of GaAs$_{0.8}$—P$_{0.2}$, lies in the fact that the sensitivity of a sensor of a uniform composition changes dramatically in the same range of pressures of 0 to 40 kilobars (from $S_{min}=2.5 \cdot 10^{-7}$ bar$^{-1}$ to $S_{max}=1 \cdot 6 \cdot 10^{-3}$ bar$^{-1}$, i.e. 6,400 times), which makes instruments comprising uniform solid solutions unfit for measurements in a board range of pressures.

What is claimed is:

1. A method for producing a heterogeneous semiconductor structure with a composition gradient by transferring a semiconductor material through the gaseous phase onto the surface of a substrate heated to a temperature of above 450° C. from a nearby solid source comprising two components AB and AC and a doping impurity, there being a difference in the temperatures of said source and said substrate, according to which method said solid source is brought to said substrate, said source comprising a plurality of adjacent main strips that extend in parallel with the edges of said source, each of said strips having its own constant ratio of said AB and AC components, the width of each of said strips being less than, or equal to the doubled distance between the surface of said source and the surface of said substrate, the first of said main strips, located near the first edge of said source, having a maximum content of said AB component, whereas said strip located at the second edge of said source has a maximum content of the AC component, the ratio of said AB and AC components in two adjacent main strips changing by a value equal to the quotient of the division of the required composition gradient value of said main layer by the width of said adjacent main strips;

said main strips being gradually brought under said substrate in the course of progressive motion of said source along said main axis and in parallel with said surface of said main axis and in parallel with said surface of said substrate, which source moves at a speed of 100 cm per hour to 0.1 cm per hour, said first main strip of said source, having a maximum content of said AB component, being the first to be brought under said substrate;

said source being stopped under said substrate, after all the main strips of said source have been brought under said substrate, and left there for a period of time required for the formation of said main semiconductor layer of a predetermined thickness.

2. A method as claimed in claim 1, whereby while forming said heterogoeneous structure with a composition gradient, the semiconductor material is transferred onto the surface of said substrate from a source comprising an additional strip whose width is at least equal to the length of said substrate along said main axis, said additional strip being adjacent to said first of said main strips and having a constant composition with a maximum content of the AB component, said additional strip being the first to be brought under said substrate, i.e. before said main strips, and being left there for a period of time required for the formation on said substrate of said additional layer of a predetermined thickness.

3. A method as claimed in claim 1, whereby while forming said heterogeneous semiconductor structure on the basis of solid solution of GaP$_x$As$_{1-x}$, the semiconductor material is transferred onto said surface of said substrate from a source comprising GaP and GaAs and having an additional group of strips located beyond said main strips, the number and composition of said additional strips corresponding to the number and composition of said main strips, the material of all said strips of the additional group being doped with an impurity producing shallow energy states to a concentration of free electrons of $8\cdot10^{17}$ to $7\cdot10^{18}$ cm$^{-3}$, whereas the material of said main strips of said source is doped to a level of $1\cdot10^f$ cm$^{-3}$, the process of gradually bringing said main strips under said substrate being accompanied by additionally doping said layers of said heterogeneous structure that are being formed from the gaseous phase with an impurity producing deep-lying energy states, the additional doping being discontinued after all said main strips of said source have been brought under said substrate, whereupon said strips of the additional group are brought under said substrate and left there for a period of time required for the formation of said main semiconductor layer of a predetermined thickness.

* * * * *